US00PP15681P2

(12) United States Plant Patent
Groot-Boon

(10) Patent No.: US PP15,681 P2
(45) Date of Patent: Mar. 22, 2005

(54) ***LOBELIA* PLANT NAMED 'KIELOWA'**

(50) Latin Name: *Lobelia×hybrida*
Varietal Denomination: Kielowa

(75) Inventor: Linda Groot-Boon, Hem (NL)

(73) Assignee: Kieft Bloemzaden B.V., Venhuizen (NL)

( * ) Notice: Subject to any disclaimer, the term of this patent is extended or adjusted under 35 U.S.C. 154(b) by 74 days.

(21) Appl. No.: 10/747,789

(22) Filed: Dec. 29, 2003

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—C. A. Whealy

(57) ABSTRACT

A new and distinct cultivar of *Lobelia* plant named 'Kielowa', characterized by its low-mounding and trailing plant habit; freely branching habit; dense and bushy plant form; vigorous growth habit; freely and continuous flowering habit; and relatively large white-colored flowers.

1 Drawing Sheet

Botanical classification/cultivar designation: *Lobelia×hybrida* cultivar Kielowa.

BACKGROUND OF THE INVENTION

The present Invention relates to a new and distinct cultivar of *Lobelia* plant, botanically known as *Lobelia×hybrida*, and hereinafter referred to by the cultivar name Kielowa.

The new *Lobelia* is a product of a planned breeding program conducted by the Inventor in Venhuizen, The Netherlands. The objective of the program is to create new trailing *Lobelia* cultivars that flower continuously during the flowering season.

The new *Lobelia* originated from a self-pollination made by the Inventor of a proprietary selection of *Lobelia× hybrida* identified as code number KA-99-1/3, not patented. The new *Lobelia* was discovered and selected by the Inventor in a controlled environment in Venhuizen, The Netherlands, during the summer of 1998 from the resultant progeny of the above-mentioned self-pollination.

Asexual reproduction of the new cultivar by terminal cuttings since the fall of 1998 at Venhuizen, The Netherlands, has shown that the unique features of this new *Lobelia* are stable and reproduced true to type in successive generations.

SUMMARY OF THE INVENTION

Plants of the cultivar Kielowa have not been observed under all possible environmental conditions. The phenotype may vary somewhat with variations in environment such as temperature and light intensity without, however, any variance in genotype.

The following traits have been repeatedly observed and are determined to be the unique characteristics of 'Kielowa'. These characteristics in combination distinguish 'Kielowa' as a new and distinct cultivar:

1. Low-mounding and trailing plant habit.
2. Freely branching habit; dense and bushy plant form.
3. Vigorous growth habit.
4. Freely and continuous flowering habit.
5. Relatively large white-colored flowers.

Plants of the cultivar Kielowa can be compared to plants of the parent selection. However in side-by-side comparisons conducted by the Inventor in Venhuizen, The Netherlands, plants of the new *Lobelia* and the parent selection differed in the following characteristics:

1. Plants of the new *Lobelia* were more trailing in plant habit than plants of the parent selection.
2. Plants of the new *Lobelia* flowered for a longer period of time than plants of the parent selection.
3. Plants of the new *Lobelia* had larger flowers than plants of the parent selection.
4. Flower color of plants of the new *Lobelia* was whiter than flower color of plants of the parent selection.

Plants of the cultivar Kielowa can also be compared to plants of the cultivar Weslowei, disclosed in U.S. Plant Pat. No. 12,708. However in side-by-side comparisons conducted by the Inventor in Venhuizen, The Netherlands, plants of the new Lobelia and the cultivar Weslowei differed in the following characteristics:

1. Plants of the new *Lobelia* were more vigorous than plants of the cultivar Weslowei.
2. Plants of the new *Lobelia* flowered earlier and more continuously than plants of the cultivar Weslowei.
3. Plants of the new *Lobelia* had larger flowers than plants of the cultivar Weslowei.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Lobelia*.

The photograph at the top of the sheet comprises a side perspective view of typical flowering plant of 'Kielowa' grown in a container.

The photograph at the bottom of the sheet is a close-up view of typical flowers and leaves of 'Kielowa'.

DETAILED BOTANICAL DESCRIPTION

Plants used in the aforementioned photographs and following description were grown under greenhouse conditions which closely approximate commercial production conditions during the summer and fall in Lompoc, Calif. Rooted young plants were grown in 15.25-cm containers in a polycarbonate-covered greenhouse and were about 13 weeks from planting when the photographs and description were taken. During the production of the plants, day temperatures ranged from 21 to 27° C., night temperatures ranged from 16 to 18° C. and light levels ranged from 5,000 to 9,000 foot-candles. In the following description, color references are made to The Royal Horticultural Society Colour Chart, 1995 Edition, except where general terms of ordinary dictionary significance are used.

Botanical classification: *Lobelia×hybrida* cultivar Kielowa.

Parentage: Self-pollination of a proprietary selection of *Lobelia×hybrida* identified as cide number KA-99-1/3, not patented.

Propagation:

*Type cutting.*—Terminal vegetative cuttings.

*Time to initiate roots, summer.*—About 12 days at 21° C.

*Time to initiate roots, winter.*—About 16 days at 21° C.

*Time to produce a rooted young plant, summer.*—About 21 days at 21° C.

*Time to produce a rooted young plant, summer.*—About 28 days at 21° C.

*Root description.*—Fine, fibrous, and white in color.

Plant description:

*Form.*—Low mounding and trailing flowering plants with relatively large white-colored flowers. Lateral shoots outwardly spreading. Freely branching habit with lateral branches forming at every node; dense and bushy. Vigorous growth habit.

*Plant height.*—About 15 cm.

*Plant diameter.*—About 54 cm.

*Lateral branch description.*—Length: About 50 cm. Diameter: About 2.5 mm. Internode length: About 3.5 to 4 cm. Cross-section: Squarish. Texture: Slightly pubescent. Color: 146A.

*Foliage description.*—Arrangement: Alternate, simple; sessile. Length: About 3.8 cm. Width: About 1.4 cm. Shape: Roughly obovate. Apex: Acute. Base: Attenuate. Margin: Slightly serrate. Texture, upper surface: Smooth, glabrous. Texture, lower surface: Slightly pubescent. Venation pattern: Pinnate. Color: Developing foliage, upper surface: 146A. Developing foliage, lower surface: 146B. Fully developed foliage, upper surface: 146A. Fully developed foliage, lower surface: 147B. Venation, upper surface: 146B. Venation, lower surface: 147B.

Flower description:

*Flower type and flowering habit.*—Large flowers arranged singly and axillary. Flowers held outwardly. Flowers persistent. Flowering indeterminate. Freely and continuously flowering habit; about ten flowers and flower buds per lateral branch. Flowers not fragrant.

*Flower shape.*—Petals fused at base; flowers tubular and bilaterally symmetrical with three larger lower petal lobes and two upright upper petal lobes.

*Natural flowering season.*—Late winter until frost in the autumn in The Netherlands.

*Flower longevity on the plant.*—Longevity of individual flowers is highly dependent on weather conditions; typically about one week.

*Flower size.*—Diameter: About 2 cm. Depth (height): About 1.2 cm. Flower length (tube and lobes): About 2.2 cm. Tube length: About 1.6 cm. Throat diameter, distal end: About 3 mm. Tube diameter, proximal end: About 2 mm.

*Flower buds.*—Length: About 1.2 cm. Diameter: About 4 mm. Shape: Roughly obovate. Color: 145C.

*Petal lobes.*—Arrangement: Single whorl of five petals, fused; three larger lower petal lobes and two smaller upper petal lobes. Length, upper lobes: About 5 mm. Length, lower lobes: About 9 mm. Width, upper lobes: About 3 mm. Width, lower lobes: About 6 mm. Shape, upper and lower lobes: Ovate. Apex, upper lobes: Cuspidate. Apex, lower lobes: Rounded. Margin, upper and lower lobes: Entire. Texture, upper and lower lobes, upper and lower surfaces: Smooth, satiny. Color, upper and lower lobes: Developing flowers, upper and lower surfaces: 155D. Fully developed flowers, upper and lower surfaces: More white than 155D. Throat: 155D; tow tiny spots at top of throat, 145A. Tube: 155D.

*Sepals.*—Arrangement: Single whorl of five sepals, star-shaped calyx. Length: About 5 mm. Width: Less than 1 mm. Shape: Narrowly lanceolate to needle-like. Apex: Acuminate. Margin: Entire. Texture, upper and lower surfaces: Smooth, glabrous. Color, upper and lower surfaces: 147A.

*Peduncles.*—Strength: Flexible and wiry, flowers held outwardly. Length: About 2.8 to 3.6 cm. Diameter: Less than 1 mm. Angle: About 45° from vertical. Color: 146A.

*Reproductive organs.*—Stamens: Quantity per flower/arrangement: About five, anthers fused. Anther length: Less than 1 mm. Anther color: More gray than 79D. Pollen amount: Scarce. Pollen color: 10A. Pistils: Quantity per flower: One. Pistil length: About 7 mm. Stigma shape: Tri-lobed; fused. Stigma color: 156B. Style length: About 4 mm. Style color: 144B. Ovary color: 144A.

*Seed/fruit.*—Seed and fruit production have not been observed.

Disease/pest resistance: Plants of the new *Lobelia* have not been noted to be resistant to pathogens and pests common to *Lobelia*.

Weather tolerance: Plants of the new *Lobelia* have exhibited good tolerance to rain and wind and to tolerate temperatures from 4 to about 28° C.

It is claimed:

1. A new and distinct cultivar of *Lobelia* plant named 'Kielowa', as illustrated and described.

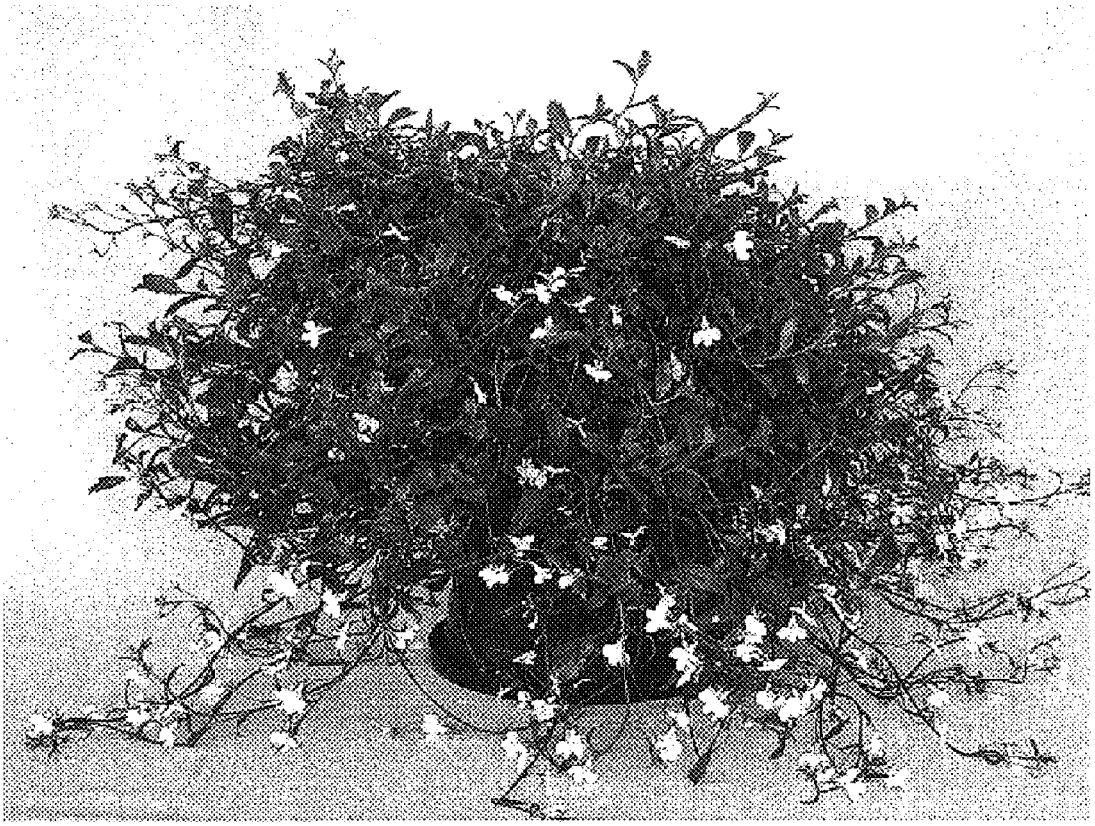
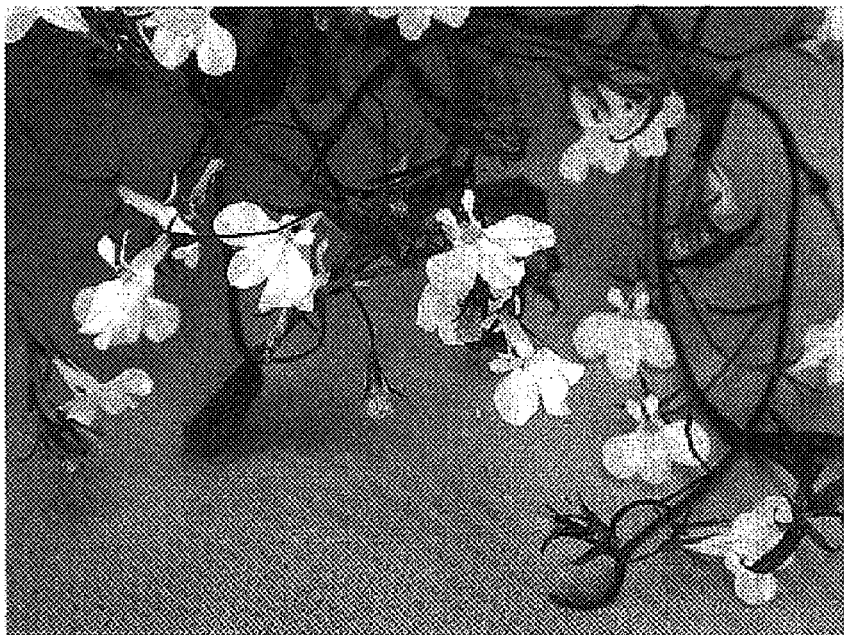

* * * * *